US011490975B2

(12) United States Patent
Kwok et al.

(10) Patent No.: US 11,490,975 B2
(45) Date of Patent: Nov. 8, 2022

(54) ROBOTIC CATHETER SYSTEM FOR MRI-GUIDED CARDIOVASCULAR INTERVENTIONS

(71) Applicant: VERSITECH LIMITED, Hong Kong (CN)

(72) Inventors: Ka Wai Kwok, Hong Kong (CN); Ziyang Dong, Hong Kong (CN); Ziyan Guo, Hong Kong (CN); Kin Chung Denny Fu, Hong Kong (CN); Kit Hang Lee, Hong Kong (CN); Chim Lee Cheung, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 456 days.

(21) Appl. No.: 15/630,406

(22) Filed: Jun. 22, 2017

(65) Prior Publication Data
US 2017/0367776 A1    Dec. 28, 2017

Related U.S. Application Data

(60) Provisional application No. 62/354,211, filed on Jun. 24, 2016.

(51) Int. Cl.
*A61B 34/35* (2016.01)
*A61B 34/30* (2016.01)
(Continued)

(52) U.S. Cl.
CPC .............. *A61B 34/35* (2016.02); *A61B 5/055* (2013.01); *A61B 18/1492* (2013.01);
(Continued)

(58) Field of Classification Search
CPC ......... A61B 34/35; A61B 34/30; A61B 34/70; A61B 90/37; A61B 5/055; A61B 18/1492;
(Continued)

(56) References Cited

U.S. PATENT DOCUMENTS 5,943,914 A * 8/1999 Morimoto .............. A61B 34/76
414/2
6,280,385 B1 * 8/2001 Melzer .................. A61B 5/055
324/318
(Continued)

FOREIGN PATENT DOCUMENTS

| CN | 102625669 A | 8/2012 | |
| WO | 2016057778 A1 | 4/2016 | |
| WO | WO-2016057778 A1 * | 4/2016 | ............. A61B 34/30 |

OTHER PUBLICATIONS

Mikaiel, S., et al. "Real-time MRI-guided Interventions Using Rolling-Diaphragm Hydrostatic Actuators," ISMRM 24th Annual Meeting 2016. vol. 24 p. 1-3 (Year: 2016).*

(Continued)

*Primary Examiner* — Catherine B Kuhlman
*Assistant Examiner* — Sean A Frith
(74) *Attorney, Agent, or Firm* — Idea Intellectual Limited; Margaret A. Burke; Sam T. Yip

(57) ABSTRACT

MRI-guided robotics offers possibility for physicians to perform interventions remotely on confined anatomy. While the pathological and physiological changes could be visualized by high-contrast volumetric MRI scan during the procedure, robots promise improved navigation with added dexterity and precision. In cardiac catheterization, however, maneuvering a long catheter (1-2 meters) to the desired location and performing the therapy are still challenging. To meet this challenge, this invention presents an MRI-conditional catheter robotic system that integrates intra-op MRI, MR-based tracking units and enhanced visual guidance with catheter manipulation. This system differs fundamentally from existing master/slave catheter manipulation systems, of which the robotic manipulation is still challenging due to the very limited image guidance. This system provides a means (Continued)

of integrating intra-operative MR imaging and tracking to improve the performance of tele-operated robotic catheterization.

24 Claims, 7 Drawing Sheets

(51) Int. Cl.
| | |
|---|---|
| A61B 18/14 | (2006.01) |
| A61B 34/00 | (2016.01) |
| A61B 90/00 | (2016.01) |
| A61B 5/055 | (2006.01) |
| A61B 5/06 | (2006.01) |
| A61B 18/00 | (2006.01) |

(52) U.S. Cl.
CPC .............. *A61B 34/30* (2016.02); *A61B 34/70* (2016.02); *A61B 90/37* (2016.02); *A61B 5/066* (2013.01); *A61B 2018/00351* (2013.01); *A61B 2018/00577* (2013.01); *A61B 2034/301* (2016.02); *A61B 2034/742* (2016.02); *A61B 2090/374* (2016.02); *A61B 2090/3954* (2016.02)

(58) Field of Classification Search
CPC ........ A61B 2034/301; A61B 2034/742; A61B 2090/374; A61B 2090/3954; A61B 5/066; A61B 2018/00351; A61B 2018/00577
See application file for complete search history.

(56) References Cited

U.S. PATENT DOCUMENTS

| | | | | |
|---|---|---|---|---|
| 8,182,494 | B1* | 5/2012 | Yencho | A61B 1/00131 600/207 |
| 2006/0265049 | A1* | 11/2006 | Gray | A61F 2/91 623/1.16 |
| 2007/0265690 | A1* | 11/2007 | Lichtenstein | A61B 90/36 607/116 |
| 2012/0078080 | A1* | 3/2012 | Foley | A61B 34/30 600/411 |
| 2012/0184955 | A1* | 7/2012 | Pivotto | A61B 34/74 606/41 |
| 2012/0253340 | A1* | 10/2012 | Stevenson | A61N 1/05 606/33 |
| 2013/0123802 | A1* | 5/2013 | Comber | A61B 34/30 606/130 |
| 2013/0190726 | A1* | 7/2013 | Kesner | A61M 25/0105 604/510 |
| 2013/0296737 | A1* | 11/2013 | McMillan | A61B 10/02 600/562 |
| 2014/0336458 | A1 | 11/2014 | Belson et al. | |
| 2015/0065952 | A1* | 3/2015 | Pacheco | A61M 25/0113 604/95.01 |
| 2015/0279031 | A1* | 10/2015 | Cavusoglu | G06K 9/6226 382/103 |
| 2015/0305650 | A1* | 10/2015 | Hunter | A61B 5/061 600/424 |
| 2015/0338477 | A1* | 11/2015 | Schmidt | A61B 5/055 600/417 |
| 2016/0008076 | A1* | 1/2016 | Bencteux | A61M 25/0113 604/95.04 |
| 2016/0022146 | A1* | 1/2016 | Piron | A61B 90/39 600/411 |

OTHER PUBLICATIONS

Walid Saliba, et al.,"Atrial Fibrillation Ablation Using a Robotic Catheter Remote Control System," Journal of the American College of Cardiology, vol. 51, No. 25, 2008, vol. 51, No. 25, 2008, pp. 2407-2411.

Celia V.Riga, et al., "Robot-assisted Fenestrated Endovascular Aneurysm repair (FEVAR) using the Magellan system," Journal 01 Vascular and Interventional Radiology, vol. 24, pp. 191-196, 2013.
S. Ernst, et al., "Initial Experience With Remote Catheter Ablation Using a Novel Magnetic Navigation System, Magnetic Remote Catheter Ablation," Circulation, 2004;109: pp. 1472-1475.
J. F. Granada, et al., "First-in-Human Evaluation of a Novel Robotic-Assisted Coronary Angioplasty System, JACC: Cardiovascular Interventions," vol. 4, No. 4, 2001, pp. 460-465.
E. S. Gang, et al., "Dynamically Shaped Magnetic Fields Initial Animal Validation of a New Remote Electrophysiology Catheter Guidance and Control System," Circulation: Arrhythmia and Electrophysiology, vol. 4, 2011, pp. 770-777.
N. F. Marrouche, et al., "Association of Atrial Tissue Fibrosis Identified by Delayed Enhancement MRI and Atrial Fibrillation Catheter Ablation The DECAAF Study," JAMA. 2014;311(5): pp. 498-506.
H. Medical, "Vascular is One of the Fastest Growing Hospital Service Lines," Available: http://www.hansenmedical.com/sites/default/files/blob-file/HM_financial%20brochure_pages.pdf.
Govindarajan Srimathveeravalli, et al., "Design and fabrication of a robotic mechanism for remote steering and positioning of interventional devices," The International Journal of Medical Robotics and Computer Assisted Surgery, vol. 6, 2010, pp. 160-170.
S. Guo, et al., A New Catheter Operating System for Medical Applications, in Complex Medical Engineering, CME 2007, IEEE/ICME International Conference on 2007, pp. 82-86.
T. Wang, et al., "Remote-controlled vascular interventional surgery robot," The International Journal of Medical Robotics and Computer Assisted Surgery, 2010, vol. 6: pp. 194-201.
L. Cercenelli, et al., "Initial Experience With a Telerobotic System to Remotely Navigate and Automatically Reposition Standard Steerable EP Catheters," ASAIO Journal, 2010, vol. 6, pp. 194-201.
J. W. Park, et al., "Development of a Force-Reflecting Robotic Platform for Cardiac Catheter Navigation," Artif Organs, 2010, vol. 34, No. 11.
Y. Fu, et al., "Development of a Novel Robotic Catheter System for Endovascular Minimally Invasive Surgery," Proceedings of the 2011 IEEE/ICME International Conference on Complex Medical Engineering, 2011, pp. 400-405.
Y. Ganji, et al., "Robot-assisted catheter manipulation for intracardiac navigation," Int J CARS (2009), vol. 4: pp. 307-315.
J. Jayender, et al., "Wave variables based bilateral teleoperation of an active catheter," in Biomedical Robotics and Biomechatronics, 2008, BioRob 2008, 2nd IEEE RAS & EMBS International Conference on, 2008, pp. 27-32.
Y. Thakur, et al., "Design and Performance Evaluation of a Remote Catheter Navigation System," IEEE Transactions on Biomedical Engineering, 2009, vol. 56, No. 7, pp. 1901-1908.
M. Tanimoto, et al., "Telesurgery system for intravascular neurosurgery," In Medical Image Computing and Computer-Assisted Intervention—MICCAI 2000, 2000, pp. 29-39.
T. Meiss, et al., "Intravascular palpation and haptic feedback during angioplasty," in EuroHaptics Conference, 2009 and Symposium on Haptic Interfaces for Virtual Environment and Teleoperator Systems, World Haptics 2009, Third Joint, 2009, pp. 380-381.
C. J. Payne, et al., "A force feedback system for endovascular catheterization," in Intelligent Robots and Systems (IROS), 2012 IEEE/RSJ International conference on 2012, pp. 1298-1304.
European Search Report of corresponding European Patent Application No. 17814748.4 dated Dec. 10, 2019.
Ka-Wai Kwok et al., "MRI-based visual and haptic catheter feedback: simulating a novel system's contribution to efficient and safe MRI-guided cardiac electrophysiology procedures", Journal of Cardiovascular Magnetic Resonance, Jan. 16, 2014, vol. 16, No. Suppl 1, p. 050.
Yue Chen et al., "An MR-Conditional High-Torque Pneumatic Stepper Motor for MRI-Guided and Robot-Assisted Intervention", Annals of Biomedical Engineering, Jun. 24, 2014, vol. 42, No. 9, p. 1823-1833.

(56) References Cited

OTHER PUBLICATIONS

The first office action of corresponding China patent application No. 201780038970.2 dated Nov. 27, 2020.

* cited by examiner

FIG. 3
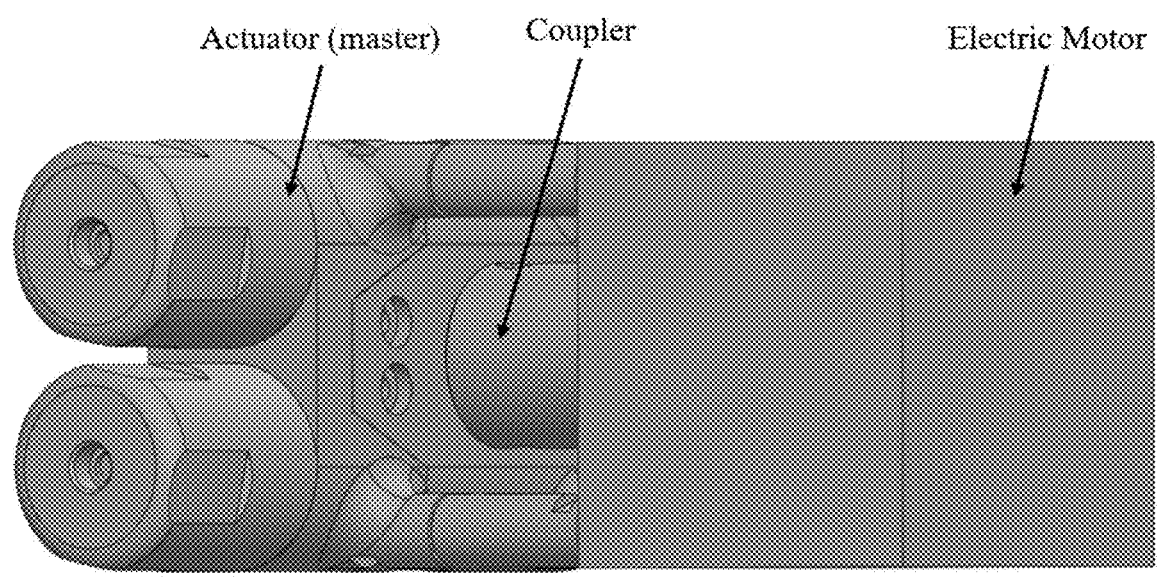
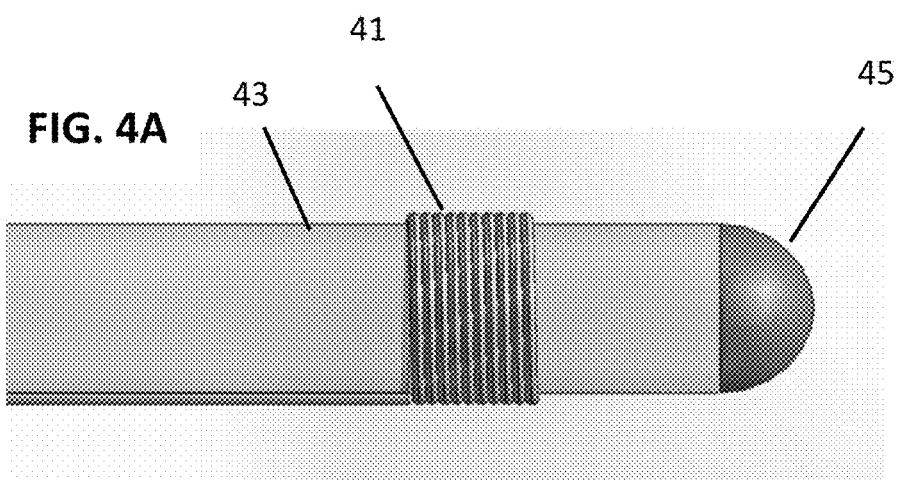
FIG. 4A

Fig. 5A
Fig. 5B
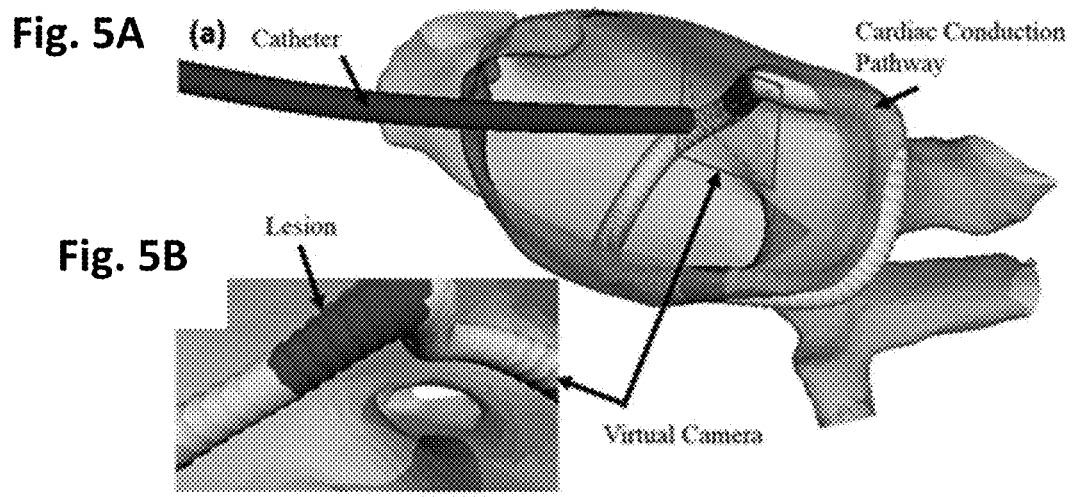
Fig. 6
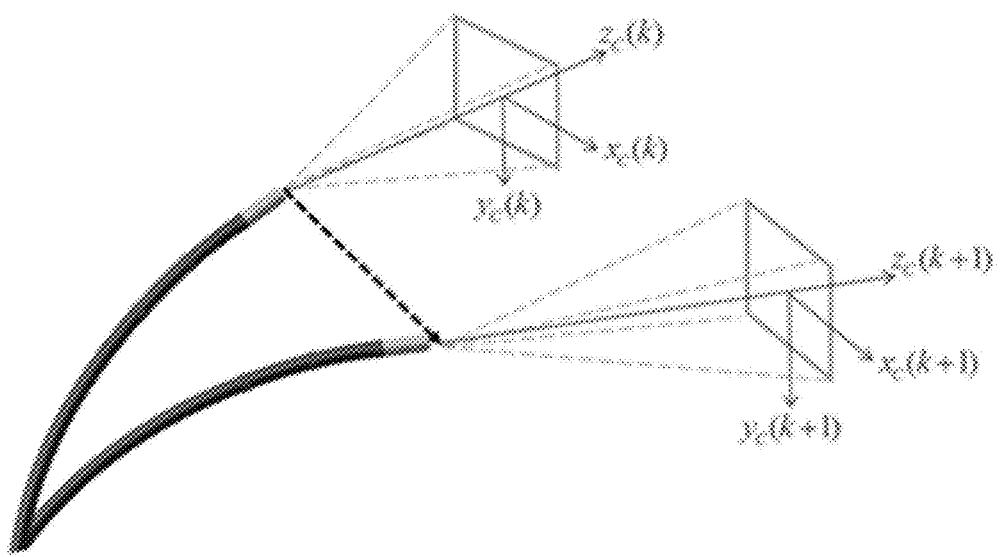

ROBOTIC CATHETER SYSTEM FOR MRI-GUIDED CARDIOVASCULAR INTERVENTIONS

CROSS-REFERENCE TO RELATED PATENT APPLICATIONS

This application claims the benefit of U.S. Provisional Application No. 62/354,211 filed Jun. 24, 2016, which is incorporated herein by reference in its entirety.

FIELD OF THE INVENTION

The present invention relates to medical robots, and particularly to surgical robots for magnetic resonance imaging (MRI)-guided interventions.

BACKGROUND OF THE INVENTION

Catheterization involves the dexterous manipulation of a long, thin and flexible medical-grade instrument to pinpoint the target anatomy for biopsy, drug delivery or lesion ablation through the transluminal, intraluminal, intracavitary or intracranial surgical approach. Such surgical manipulation could be applied on cardiovascular intervention, prostate surgery, stereotactic neurosurgery or breast biopsy.

Cardiovascular diseases, which remain the major cause of mortality in developed countries, also demand dexterous catheterization. Endovascular catheterization technologies have been embraced as a common treatment of these conditions in combination with interventional radiology and cardiology. In order to provide pre-operative diagnosis and intra-operative guidance, as well as effective catheterization, for endovascular procedures, different imaging modalities including X-ray, ultrasound, and MRI are being used.

An MRI scanner for cardiovascular intervention is a large machine generating a strong magnetic field. In an MRI room, many electrical devices must be provided with electromagnetic (EM) shielding in order to avoid interference with image acquisition. Cardiovascular EP is also a procedure requiring multiple screens of reference for delicate catheter navigation, as well as detailed instant monitoring of cardiac signal/status. It is difficult and expensive to equip multiple computer monitors/displays inside an MRI room.

One type of endovascular catheterization treatment involves catheter radio-frequency (RF) ablation procedures. The aim of such procedures is to isolate abnormal electrical impulses generated by destroying heart tissue that triggers the irregular heart rhythm. Usually it is done by making small burns in the heart tissue, so that it is unable to conduct incorrect impulses. This is done using a long thin tube (catheter) threaded into the heart chamber.

During ablation, MRI offers valuable information, i.e. clear visualization of pathological and physiological changes in the targeted anatomy (e.g. scars and edema on tissue created by catheter ablation). In particular, it offers high-contrast images of soft tissues, provides 3-D anatomic visualization and permits the visualization of infarct, ischemic and arrhythmogenic tissue ablation lesions hemorrhages, and detailed information about morphological and physiological changes in soft tissue during the procedure. However, the effective maneuvering of a long and flexible catheter (e.g. about 1.5 m) to the desired target points within a highly dynamic environment, particularly inside the heart chamber, still remains a great challenge. The challenges have drawn attention to the development of tele-operated robotic platforms, such as the well-known commercial one—Sensei® Robotic System—that improve the dexterity and accuracy of catheter manipulation for intra-cardiac intervention. The current 3-D roadmap used for catheter manipulation guidance is computed from pre-operative (pre-op) MRI or computed tomography (CT) scans. However, imaging during the intervention has proved to be of paramount importance to monitoring the physiological changes of cardiovascular tissue as a form of intra-operative (intra-op) feedback while performing responsive therapeutic procedures, such as radio-frequency (RF) ablation.

MRI offers excellent image contrast for soft tissue, forming a detailed anatomical roadmap in three dimensions, 3-D. In cardiovascular electrophysiology (EP), gadolinium enhancement T2-weighted cardiac MRI can also readily visualize the scar tissue and edema arising from successful or incomplete RF ablation during the procedure. Many research groups have already conducted numerous patient trials, and demonstrated the significant clinical value of the use of intra-op MRI, particular for cardiovascular EP in clinical routines. However, the ferromagnetic materials and conductive components in most catheter robots and steerable catheterization systems may not be used with the MRI scanner due to the strong magnetic field generated. Currently, neither any existing commercial nor research prototype of a robotic catheterization platform is MR-conditional/safe that could even navigate the medical-grade catheter. Moreover, there are many technical gaps strongly driving the demand for the development of an MRI-guided catheter robot incorporated with dexterous manipulation, enhanced intra-operative (intra-op) navigation and an intuitive human-robot control interface.

MRI offers excellent image contrast for soft tissue, forming a cardiac roadmap in 3-D. However, the development of real-time and continuous instrument tracking techniques for MRI navigation is still in its infancy. Pre-op MR or computed tomography (CT) images in 3-D are commonly acquired before surgery, and fluoroscopy is used to visualize the virtual catheter configuration during the procedure. For example, in cardiovascular EP, the 3-D position of the catheter tips inside the patient's vessel or cardiac chamber is continuously tracked using either a high-voltage or EM-based device in real-time, thus enabling formation of 3-D electro-anatomic mapping (EAM), in which the morphology is very rough and not anatomically correct. This makes navigation rather challenging. Commercial systems, such as CARTO system (Biosense Webster, Calif., USA) and the EnSite system (St. Jude Medical, MN, USA), allow the co-registration of EAM with the pre-op imaging model. However, due to the usually large disparity (>5 mm) between the tracking and image coordinates, such co-registration is very inaccurate in providing localization of the catheter relative to the imaging model. To avoid this disparity, both catheter tracking and cardiac MRI may have to take place in the same coordinate system Currently, there is no well-established robot-human interface capable of continuously registering target locations based on intra-op MR images, and guiding the effective manipulation of a long, thin, flexible catheter. Reliable catheter kinematic mapping enables the electrophysiologist to understand the catheter manipulation based on what they see, and to coordinate the manipulation accurately relative to the cardiac anatomy. Many research attempts have focused on the kinematics-based model for catheter control, in which the catheter acts as a continuum robotic structure with infinite degrees-of-freedoms (DoFs). Numbers of assumptions are required, though those are mostly inapplicable in the clinical environment coupled with rapid cardiac motion and pulsatile blood flow. These existing methods are incapable of providing steady, smooth and consistent control mapping in a dynamic surgical environment. Thus an adaptive kinematic control framework would constitute an improvement on these existing methods.

SUMMARY OF THE INVENTION

The present invention relies upon robot motion driven by an MR-safe actuation unit. The actuator is fabricated with MR-safe materials. As it is actuated by fluid-based power, the whole unit is MR-safe and provides minimal imaging interference in the MR environment. The actuator comprises pairs of hydraulic/pneumatic piston-actuators connected with one or more than one long flexible tubes (5-10 meters). Each piston-actuator has one or more than one rolling diaphragm, piston and cylinder. The two piston-actuators are connected to each other by tubes that are filled with pressurized fluid. The rolling diaphragms act as flexible seals. When the fluid volume in one cylinder is changed, it induces a pressure difference on the wall of the rolling diaphragm and pushes the piston into a translational motion. The two or more piston-actuators are assembled together such that the translational motions of the pistons are transferred to rotational motion by a converter mechanism for linear-to-rotary motion. The displacements of the piston-actuators are in parallel or in a radial direction.

To vary the rotational range, alternatives can be adopted. For example, the two piston-actuators can be placed at an acute angle or a flexible connection between piston and gear (e.g. a belt) can be utilized to enable various diameters of the gear in-between, which transfers the translational to rotary motion. Three or more piston-actuators can be placed radially or axially to provide continuous bi-directional infinite rotation.

Robot navigation of the cardiac catheter uses MR-based tracking units. The tracking unit is a micro circuit comprising resistor, inductor, and capacitor (RLC) elements, which can operate as MRI-based active or semi-active signal markers and enable the real-time, frequent, and continuous sampling of instrument positional tracking information with respect to (with regard to) the image coordinates. While all the existing prototypes require manual selection of passive landmarks on MR images, e.g. fiducial markers capsulized with gadolinium/vat or optical positional tracking devices. This small coil unit enables instrument tracking with high rate position sampling (at >10 Hz), and with low latency (<50 ms) in fine spatial resolution of ≤0.6×0.6×0.6 mm$^3$ using appropriate MR tracking sequences. It allows virtual augmentation of an instrument configuration on the MR imaging model precisely in real time.

The present invention incorporates MR-tracking with robotic systems, enabling the real-time positional data of the catheter/instruments to close the control loop of robot navigation. An adaptive kinematic control framework is also incorporated to provide online estimation of the motion mapping from the robot actuation to the tip displacement. This update is achieved by the means of a stochastic method that solely depends on real-time measurements, namely the tracked position of the catheter tip, but without having any prior knowledge or pre-acquisition of accurate catheter kinematics. This control framework aims at significant improvement of hand-eye coordination during the catheter manipulation/navigation.

Currently, neither any existing commercial robotic catheterization platform, nor any research prototype providing full manipulation of catheter, can be safely operated in an MRI environment. There is also no well-established robot-human interface capable of continuously updating a surgical roadmap and catheter location based on MR images. The system of the present invention is integrated with MRI-safe/conditional actuation, MR-based tracking system, and intraoperative MRI for image-guided intervention. Through the use of the present catheter robot, a precise and real-time visual feedback to the operator is provided during the catheter/instrument navigation under the MRI. Sharing the same MR-tracking coordinates with the same MR images can guarantee correct alignment of the virtual catheter/instrument configuration relative to the cardiac imaging models, thereby being of benefit to all kinds of MRI-guided catheter interventions.

With the present invention the operator can be located at a distance from the MRI and patient. However, the remotely-operated catheter robot will allow the electrophysiologist to control the catheter in a control room with sufficient number of monitors/displays as many in the conventional EP and without being subject to the MRI energy.

In the present invention, a robot is provided which is capable of conducting catheter tracking in the same imaging coordinate system as MR images. Therefore, such real-time positional tracking data can act as the feedback data for closing the control loop of the robot navigation. 3-D co-registration between the tracking and imaging coordinates is no longer required, as in many conventional image-guided interventions. This robotic close-loop system incorporated with MR-based tracking will also be a benefit to all kinds of MRI-guided robot-assisted interventions.

This invention represents a major step in achieving several goals: i) enhancing the catheter/instrument manipulation and access to the region of surgical interest, thus decreasing the chances of disease recurrence, compensating for the cost of using MRI and reducing the overall expenditure; ii) improving the safety of catheter/instrument navigation, thereby decreasing the rates of undesired or inadvertent tissue damage; and iii) enhancing the catheter/instrument control, thus facilitating a shorter learning curve for the operator and better treatment in more complex cases.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 3 illustrates a perspective view of an MR-safe two-piston actuator master unit coupled to an electric motor;

FIG. 4A illustrates an example of a coil of an MR-based tracking unit mounted on the catheter tip of FIG. 1;

FIG. 5A illustrates a 3-D cardiac roadmap (dark shaded area) with lesion targets (yellow) indicated on the pulmonary vein ostium;

FIG. 5B illustrates a virtual camera view that is augmented from the point of view of the catheter tip;

FIG. 6 illustrates virtual camera coordinates aligned with the catheter tip;

DETAILED DESCRIPTION OF EXEMPLARY EMBODIMENTS OF THE INVENTION

Figure 1:
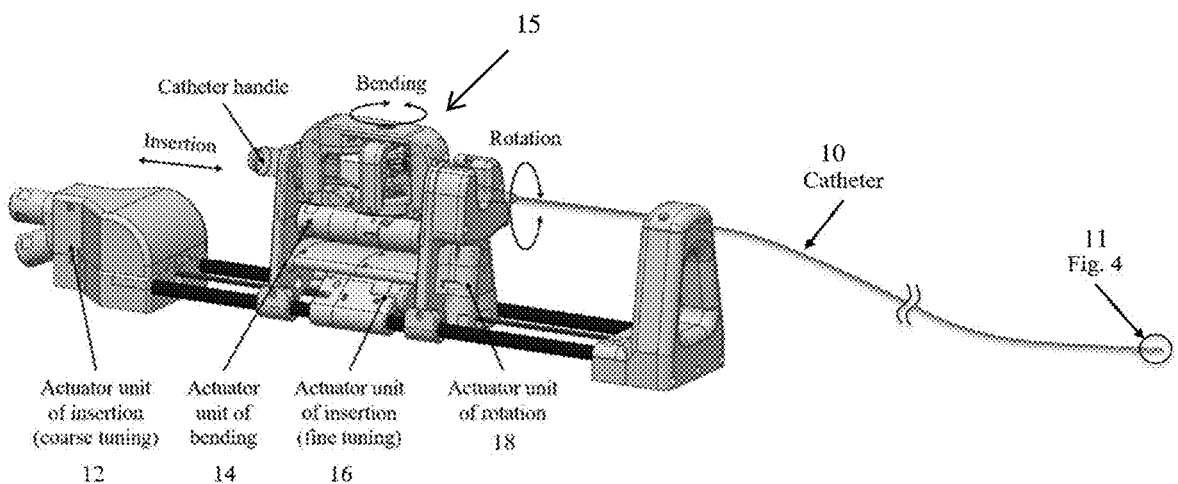
FIG. 1 illustrates the mechanism of an MR-conditional catheter robot.

The current invention is a surgical catheter robot for MRI-guided intervention in endovascular procedures in a remote way. The components of the present invention could also be composed of and integrated with various designs of other robotic platforms used for interventions which are benefited from intraoperative guidance by MRI, such as neurosurgery, prostate surgery or breast biopsy. In particular, FIG. 1 shows a robot guide for a catheter 10, whose tip 11 is shown enlarged in FIG. 4. The catheter is guided through the body of a patient. The robot is made of MRI-safe/conditional materials (or any non-ferromagnetic materials, e.g. plastics/polymers). The robot comprises a main robot body 15 and actuators 12, 14, 16 and 18, that provide 3 degrees-of-freedom (DoFs) motion, i.e. allowing linear translational, rolling and steering control over the catheter.

For achieving the catheter pushing/pulling motion, the two actuator units 12, 16 serve separately for coarse movement and its fine tuning. The actuator unit for coarse linear motion 12 is connected to a manipulator platform by a long-stroke transmission mechanism (e.g. a belt, a screw), while the other unit 16 for fine tuning is directly geared to the unit. This design enables the flexible adjustment of the transmission ratio, and also the insertion range. Such fine tuning guarantees the corresponding motorized DoF have high accuracy and quick response. The robot also has an actuator 14 which is used to bend the catheter, e.g. via adjusting the knob on the catheter handle, pulling the catheter tendons or pushing/pulling the catheter inner/outer tubes. An actuator 18 acts to rotate the catheter by rotating the entire catheter mounting platform.

The actuators are made of MRI-safe/conditional materials (e.g. plastics/polymers) and are driven by fluid, i.e. they operate by hydraulics/pneumatics, which provide bidirectional rotation/translation. See FIG. 2A. Thus it is safe to use them in an MRI system because they are not affected by the MRI fields and will not generate any EM waves or otherwise interfere with the operation of the MR imaging.

The master or slave side of the actuator unit in the robot comprises two or more piston-actuators. For an actuator with two piston-actuators, a gear or a flexible connection (e.g. belt) is used to transfer the translational motion to the bi-directional rotation within a range. Backlash is minimized for it, because its gears or a flexible connection are preloaded. The actuator with two piston-actuators has a precise and short-range of motion, which is suitable for the bending of the catheter and fine tuning of the insertion of the robot. For the actuator with three or more piston-actuators (FIG. 2C), the piston-actuators are placed radially or axially against an eccentric shaft. This design can provide an infinite range of bidirectional continuous rotation and allow for separate control of the piston-actuators. This design is suitable for implementation in robot DoFs that require a long operational range, e.g. catheter rotation and coarse insertion.

The actuator unit incorporated in the robot is connected with another symmetric actuator unit or separate piston units at the master side by several hydraulic/pneumatic tubes. The actuators contain rolling diaphragms and/or other types of seals (e.g. sliding contact seals) to provide fluid sealing. For actuators providing sealing with rolling diaphragm, friction loss is low during the transmission. There are, at least, two alternatives to drive the slave actuator at the master side:

1) The slave actuator is connected with another symmetric master actuator at a master side by two or more tubes. An electric motor at the master side drives the master actuator or pistons, while the slave ones replicate the motion simultaneously through the hydraulic/pneumatic transmission.

2) The slave actuator is connected with separate piston units at the master side. Each piston pair is driven by electric motors at the master side respectively. A dynamic model of the actuator can be developed to describe the transmission between the master and slave side. Based on the model, control algorithms are implemented to generate desired output motion and torque at the master side.

Figure 2A:
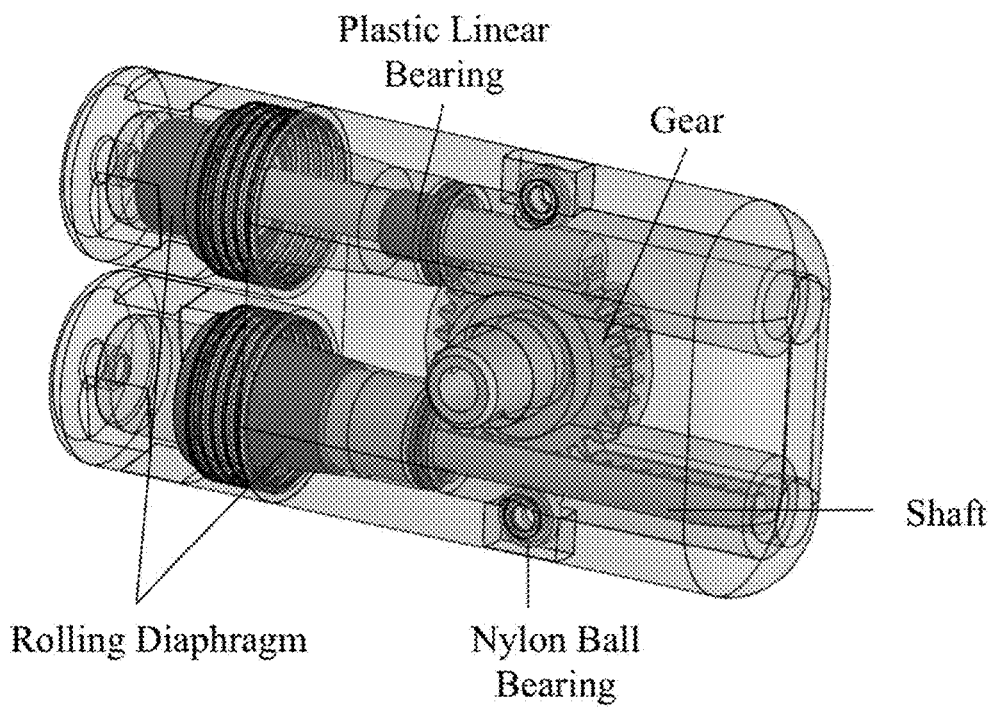
FIG. 2A illustrates the internal mechanism of an MR-safe actuator master/slave unit with two piston-actuators in parallel.
Figure 2B:
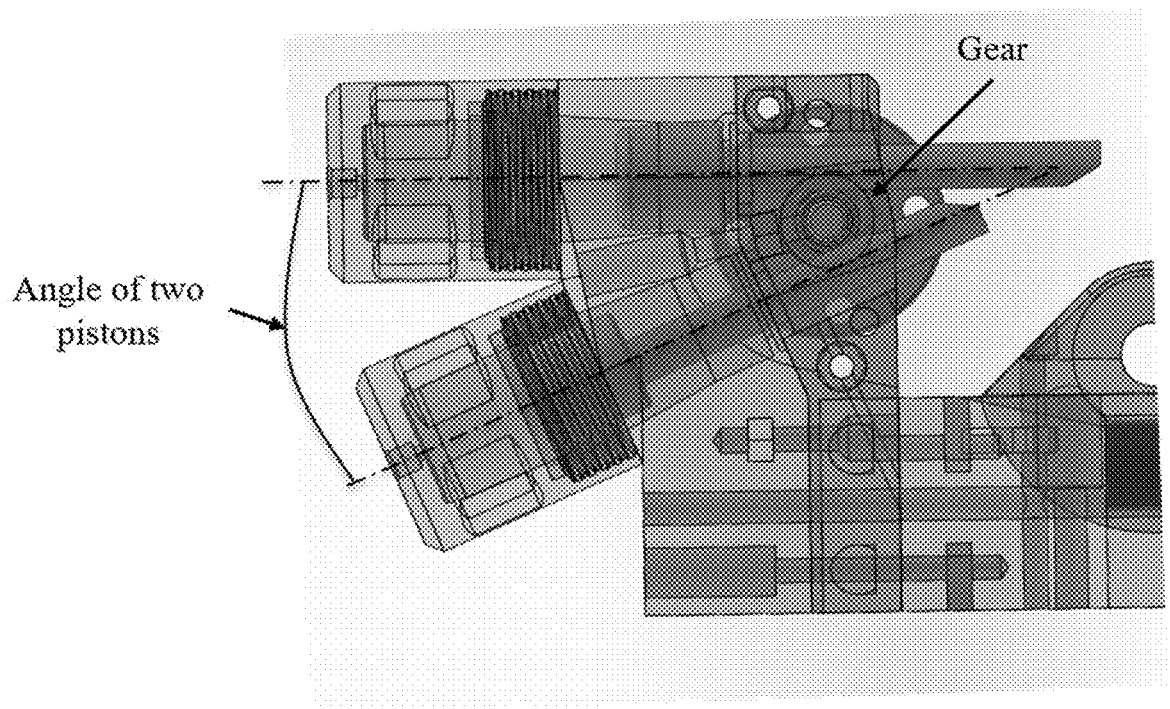
FIG. 2B illustrates the internal mechanism of an MR-safe actuator slave unit with two piston-actuators at an acute angle.
Figure 2C:
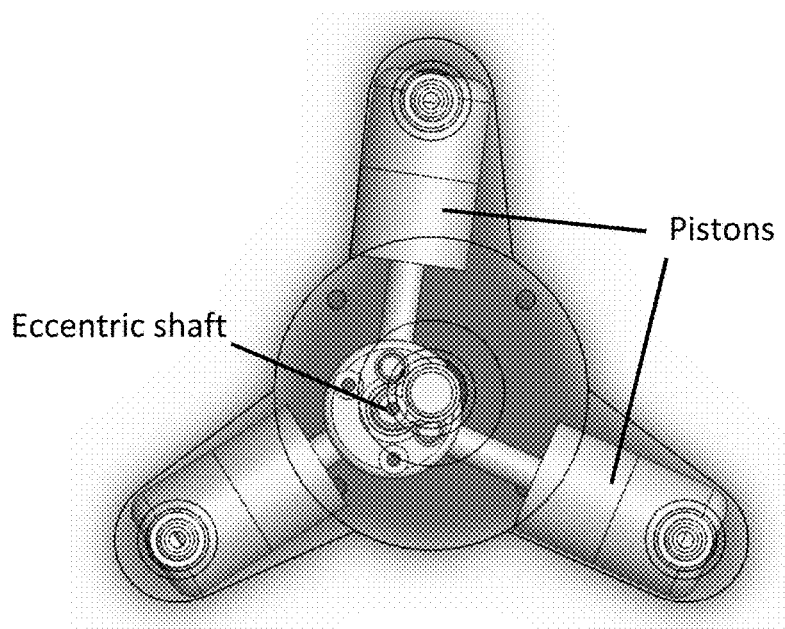
FIG. 2C illustrates the internal mechanism of an MR-safe actuator slave unit with three piston-actuators placed radially.

In this way, several functions can be achieved for the actuator, such as steady or controllable output velocity/torque and backlash compensation. The master unit is shown in FIG. 2A. This actuation transmission features high stiffness, wide bandwidth and low friction. As such, the operator can obtain a finer motion for the manipulation of the catheter/instrument.

The catheter robot navigation is provided by multiple tracking units, each of which consists of a micro RLC coil circuit as shown in FIG. 4A, which can serve as an MRI-based signal marker. This coil structure can be wound around the catheter/needle surface 43 near the tip 45 of the catheter. As an alternative it can be fabricated directly on a flexible film capable of being attached onto the tracking points (e.g. near the tip of the catheter). The tracking unit acts like a radiofrequency (RF) antenna to pick up the MR gradient signal, or an inductor component that resonates with the signal transmitted to the MRI scanner receiver. Therefore, either active or semi-active MR tracking can be incorporated into the system. By resonating at the same MR-signal frequency, the tracking unit enables the real-time (i.e. low latency <50 ms), frequent and continuous sampling (at >10 Hz) of the instrument positional tracking, as well as the instrument configuration, with respect to the MR-image coordinates. The resolution can be ≤0.6×0.6×0.6 $mm^3$.

Figure 4B:
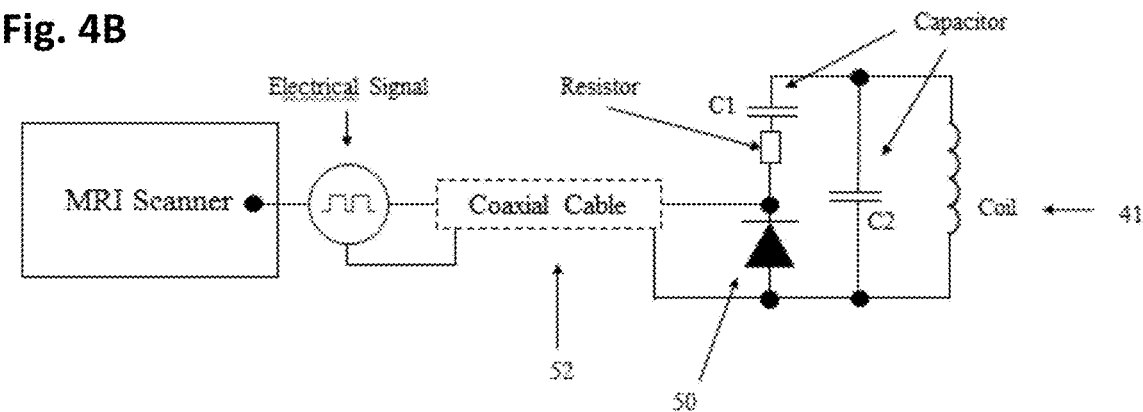
FIGS. 4B and 4C illustrate a coil tracking circuit and alternative arrangements for altering the state of the circuit.

In addition to the coil shown in FIG. 4A, the MR-based tracking unit includes additional elements so as to form an individual RLC coil circuit as shown in FIG. 4B. The entire circuit is mounted on the catheter adjacent its tip. The MR-based tracking unit can be switched between multiple states, such that it can appear on the display as a bright spot in the MR images or provide positional information to the robotic system. The multiple states can be altered by changing the electrical characteristics of the coil circuit (e.g. inductance, capacitance, resistance) during MR scanning. The alternation of the electrical characteristics can be achieved by incorporating a diode 50 within the circuit. This diode 50 is connected to the MRI scanner system by a coaxial electrical cable 52. See FIG. 4B. By applying an electrical current through the coaxial electrical cable to the photodiode the MR-based tracking unit is switched on and off.

Figure 4C:
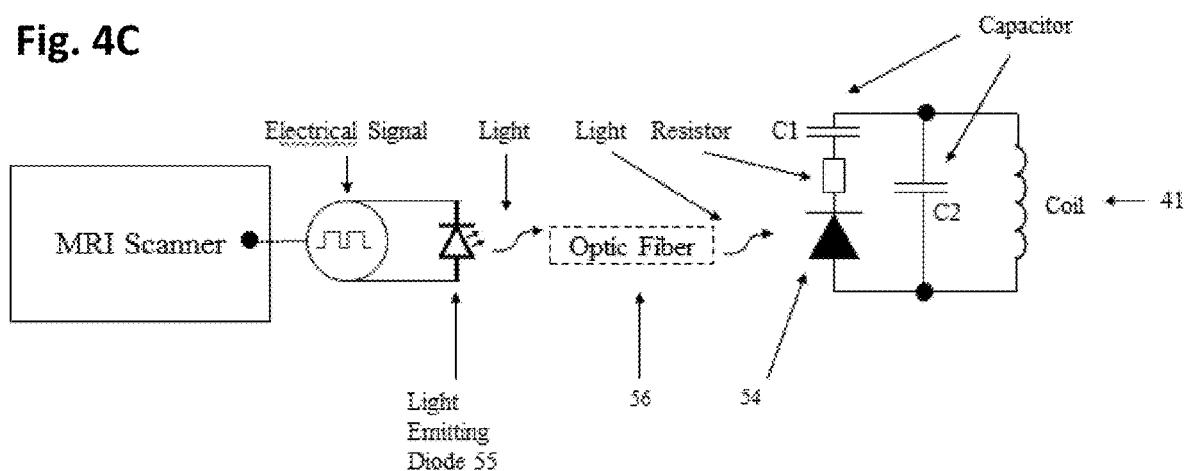

As an alternative the alternation of the electrical characteristics can be achieved by connecting the MR-based tracking unit with either a PIN photodiode or a photo-resistor 54 that is further connected to the MRI scanner system with optic fiber 56 as shown in FIG. 4C. By applying light from LED through the optic fiber to the PIN photodiode or the photo-resistor the electrical characteristics of the MR-based tracking unit can be switched between multiple states.

The present invention can provide a graphical interface to show the visual guidance for the navigation of the catheter or other parts of the embodiments. The graphical interface can display the pre-operative or intra-operative MR images in 2-D or 3-D space. This allows a physician to see the tissue that is targeted for treatment (e.g. ablation) prior to and/or during treatment (e.g. ablation). The graphical interface can also display the 3-D EAM, electrocardiogram (ECG) and/or other physiological data related to the patent.

One or multiple virtual 3-D roadmaps of the patient anatomy obtained by MR imaging or other imaging techniques can be overlaid on the graphical interface with or without the MR image slices, as shown in FIGS. 5A and 5B. This 3-D roadmap can also be overlaid with virtual 3-D models of the catheter to locate the measured catheter position inside or outside the patient's body. The positional information of the catheter can be provided by one or multiple MR-based tracking coils 41, or/and other position tracking techniques. The graphical display can also overlay the pre-planned ablation targets or/and the completed RF ablation lesion, which are illustrated as light and dark targets along the cardiac conduction pathway in FIGS. 5A and 5B.

The graphical interface can display the abovementioned visual information in an individual or combined manner as 3-D visual guidance in one or multiple viewing perspectives. FIG. 5A illustrates an example of a viewing perspective that displays the virtual catheter and 3-D roadmap of the cardiovascular tissue, as well as its ablated status. The targets, which are shown dark in the drawings, depict the completion of RF ablation obtained from the intra-operative MR images.

FIG. 5B illustrates an endoscopic view which is virtually rendered from the view point of catheter distal tip (see dotted lines in FIG. 5A) to the cardiovascular roadmap in 3-D. FIG. 6 is an illustration of virtual camera coordinates aligned with the catheter tip. The virtual endoscopic view is particularly reliable and convenient when the position of the catheter tip is tracked by the MR-signal in the image coordinates, as it shares the same image coordinate system with the 3-D roadmap constructed by the intra-operative MR images. This visual feedback technique combined with MR-based tracking can eliminate the need for extra relative registration between the positional tracking coordinate and the MR imaging coordinates, leading to a more accurate visual feedback.

Figure 7:
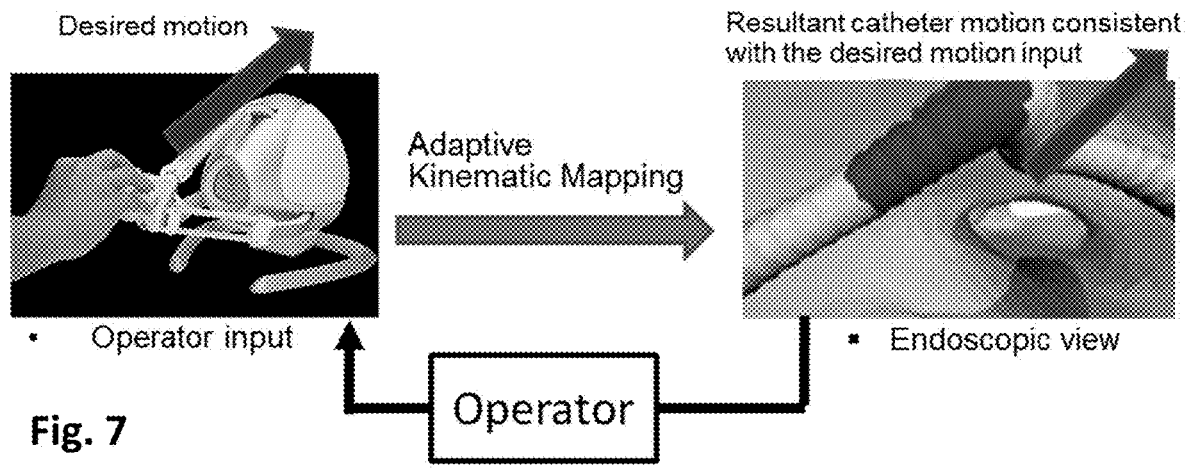
FIG. 7 illustrates a diagram of the adaptive kinematic control framework.

The embodiments of the invention can be operated automatically or manually by a motion input device (e.g. joystick as shown in FIG. 7) that can remotely control the actuation of the robotic catheter. The robot operator can stay in the control room to tele-manipulate the robot catheter through the abovementioned visual interface.

By tracking the catheter tip location continuously online in the MRI, the embodiment of the present invention can automatically realign the coordinates between the motion input device and the movement of the endoscopic view, thus enhancing the hand-eye coordination in tele-manipulation of the catheter. The operator can find that the movement of the endoscopic view is approximately consistent with his/her hand motion on the motion input device. Thus, the interface enables direct mapping from the motion input to the movement of the endoscopic view.

The present adaptive kinematic control framework can be integrated into a single piece, but can be operated in multiple pieces of software in different processors, but that would require communications between the processors.

Figure 8:
FIG. 8 is a photograph of the robot next to the MRI phantom with both placed inside the MRI scanner bore.

An imaging phantom is a specially designed object that is scanned or imaged in the MR field to evaluate, analyze and tune the performance of the MRI device. Phantoms are more readily available and provide more consistent results than the use of a living subject and likewise avoid subjecting a living subject to direct risk. FIG. 8 is a photograph of the robot next to an MRI phantom with both placed inside the MRI scanner bore.

Figure 9:
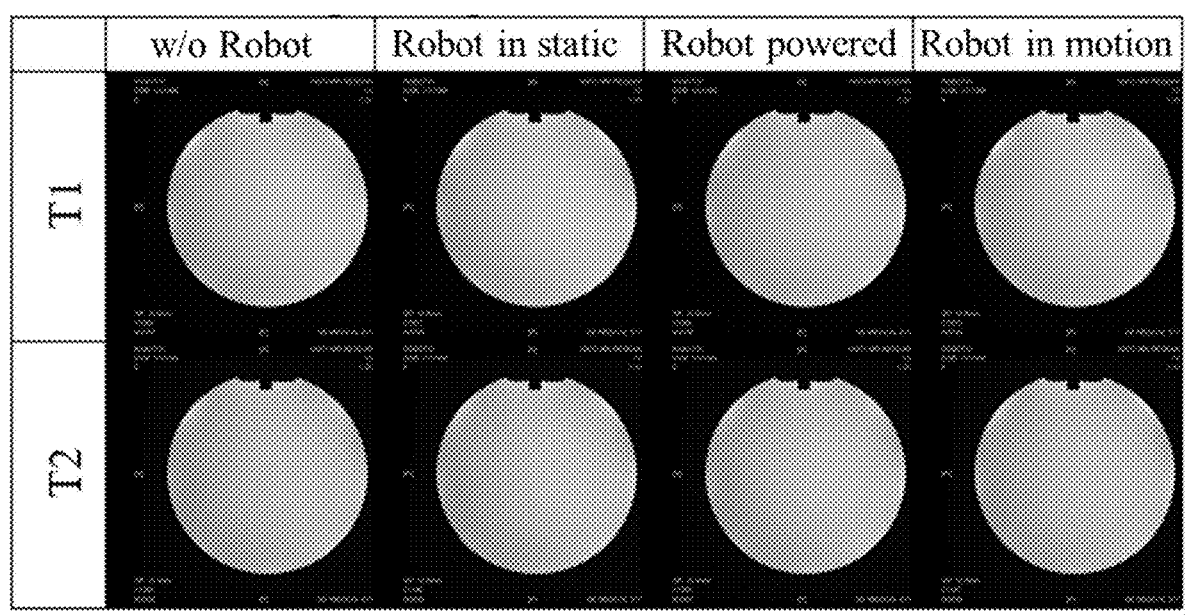
FIG. 9 illustrates MRI images of the phantom under two image sequences (T1-weighted and T2-weighted), when the catheter robot is placed at an isocenter and operated under different conditions.

FIG. 9 illustrates MRI images of the phantom under two image sequences (T1-weighted and T2-weighted) when the catheter robot is placed at an isocenter beside the phantom and operated under different conditions. The first condition is "w/o Robot", i.e. only the phantom is placed in the scanner. The second condition is "Robot in static", i.e. the robot has been introduced into the scanner, but all of the power is off. In the third condition, which is "Robot powered", the electric power is on, but the robot is static. The fourth condition is "Robot in motion," which is when the robot is in its normal operation state. This sequence shows that the robot does not affect the imaging of the phantom.

This system is integrated with MRI-compatible actuation, MR tracking, and the 3-D surgical roadmaps registered with intra-operative MR images. It provides the operator with a consistent motion reference to maneuver the catheter tip aiming at the desired lesion target for ease of navigation. In other words, the operator finds that movement of the virtual endoscopic view is approximately consistent with his/her hand motion on joystick. The successfully developed components of this system can be further implemented in other robot-assisted interventions, particularly those using flexible continuum instrument navigated in dynamic tissue environment under MRI.

While the present invention has been particularly shown and described with reference to preferred embodiments thereof; it will be understood by those skilled in the art that various changes in form and details may be made therein without departing from the spirit and scope of the invention.

What we claimed is:

1. A robotic MRI-guided instrument placement system, comprising:
   a robot body made of a non-ferromagnetic and MR-safe material;
   a plurality of actuators connected to the robot body and made of non-ferromagnetic and MRI-safe material, the plurality of actuators using fluid-based transmission to cause an instrument to perform at least one of push forward, pull backward, rotate clockwise, rotate counterclockwise, or bend right and bend left; wherein the plurality of actuators include a master actuator or a slave actuator, and wherein the master actuator or the slave actuator comprises two or more piston-actuators, each piston-actuator using at least one rolling diaphragm for fluid sealing and having a gear or a flexible connection to transfer translational motion to bi-directional rotation; and there are two actuators of the plurality of actuators that cause the robot body to push forward or pull backward with one coarse actuator providing coarse placement and one fine actuator providing fine placement and wherein the coarse actuator is connected to the robot body by a long stroke transmission mechanism, and the fine actuator is connected to the robot body through gears; and more than one MR-based tracking units mounted on a tip of the instrument, each of the MR-based tracking units including an RLC coil circuit, the MR-based tracking units being switchable between multiple states, such that a tracking unit, in one state appears as a bright spot in MM scanned images and, in another state, provides positional information;

wherein the MR-based tracking units are operated with rate position sampling greater than 10 Hz and with latency less than 50 ms with spatial resolution of less than or equal to 0.6×0.6×0.6 mm$^3$ using MR pulse tracking sequences;

a remote control for remotely directing operation of actuators;

a navigation system including a processor receiving intra-operative MM image data, the processor creating a 3-D anatomical roadmap and locating tracking units relative to anatomical features of a patient in which the instrument is placed and wherein robotic manipulation of the instrument is guided by real-time MR-based tracking and wherein 3-D tracking coordinates are the same as an MR image coordinate system; and a display for providing an endoscopic view from the tip of the instrument tracked under MM.

2. The robotic MM-guided instrument placement system of claim 1, further including an adaptive kinematic control framework.

3. The robotic MM-guided instrument placement system of claim 1, wherein the master or slave actuator comprises three or more piston-actuators arranged radially or axially and connected to an eccentric shaft, whereby an infinite range of bi-directional rotation is provided.

4. The robotic MM-guided instrument placement system of claim 1, wherein the master actuator or the slave actuator include two piston-actuators that are placed in either a parallel configuration or with an acute angle therebetween to adjust the motion range.

5. The robotic MRI-guided instrument placement system of claim 1, wherein the robotic MRI-guided instrument placement system includes the master actuator and the slave actuator, and wherein the slave actuator is connected with another symmetric master actuator at a master side by two or more tubes, and wherein an electric motor at the master side drives the master actuator, while the slave actuator replicates the motion simultaneously through a hydraulic/pneumatic transmission.

6. The robotic MRI-guided instrument placement system of claim 1, wherein the robotic MRI-guided instrument placement system includes the slave actuator, and wherein each piston-actuator in the slave actuator is connected with one corresponding piston unit at a master side, and wherein electric motors at the master side drive each piston pair respectively.

7. The robotic MM-guided instrument placement system of claim 1, wherein the processor operates to provide controls of the actuator, including motion control and torque control.

8. The robotic MRI-guided instrument placement system of claim 1, wherein a media of power transmission between master and slave actuators is pneumatic, hydraulic or a combined media of them.

9. The robotic MM-guided instrument placement system of claim 1, wherein the instrument is a catheter.

10. The robotic MRI-guided instrument placement system of claim 9, wherein each MR-based tracking unit is a wire coil which is wrapped about the catheter tip.

11. The robotic MRI-guided instrument placement system of claim 10, wherein each of the MR-based tracking units is in the shape of one of a solenoid, saddle, and planar spiral.

12. The robotic MRI-guided instrument placement system of claim 1, wherein there are multiple RLC coil circuits mounted on a tip of the instrument to provide multiple position information.

13. The robotic MRI-guided instrument placement system of claim 12, wherein the RLC coil circuits used to make each of the MR-based tracking units is fabricated with conductive metal selected from copper, gold, silver, tungsten, titanium or iron.

14. The robotic MRI-guided instrument placement system of claim 12, wherein each of the MR-based tracking units is fabricated on a flexible polymer film that is capable of being attached to the distal end of the instrument.

15. The robotic MM-guided instrument placement system of claim 14, wherein the flexible polymer film is made with one of polyimide and polyether ether ketone (PEEK).

16. The robotic MM-guided instrument placement system of claim 1, wherein the instrument is a catheter and each of the MR-based tracking units is an individual LC coil circuit mounted on the catheter adjacent its tip.

17. The robotic MM-guided instrument placement system of claim 1, wherein the multiple states can be altered by changing the electrical characteristics of the MR-based tracking units selected from inductance, capacitance, resistance during MR scanning.

18. The robotic MRI-guided instrument placement system of claim 17, wherein the alternation of the electrical characteristics is achieved by connecting each of the MR-based tracking units with a diode that is further connected to an MRI scanner system with coaxial electrical cable, and by applying an electrical current through the coaxial electrical cable to the diode to switch the MR-based tracking units on and off.

19. The robotic MRI-guided instrument placement system of claim 17, wherein the alternation of the electrical characteristics is achieved by either connecting the MR-based tracking units with a PIN photodiode or a photo-resistor that is further connected to the MRI scanner system with optic fiber, and by applying light through the optic fiber to the PIN photodiode or the photo-resistor, whereby the electrical characteristics of the MR-based tracking units can be switched between multiple states.

20. The robotic MM-guided instrument placement system of claim 1, wherein the system has a control loop and real-time MR-based positional tracking data acts as feedback data for closing the control loop for robot navigation.

21. The robotic MM-guided instrument placement system of claim 1, wherein the remote control is a motion input device located separately from the robot body so that the system can be operated remotely from an Mill machine in which the robot body is located.

22. The robotic MM-guided instrument placement system of claim 1, wherein the instrument is a catheter and the display provides an endoscopic view from the end of the catheter along with coordinate information.

23. A method of robotically guiding a flexible catheter instrument using Mill data, comprising:

providing the robotic MRI-guided instrument placement system of claim 1, positioning a patient in a bore of an MRI device along with the robot body;

creating an incision in the patient, whereby a catheter is manually delivered to a target location; assembling a catheter handle on the robot body;

powering the robot body and actuators made of non-ferromagnetic and MR-safe material, wherein the actuators use fluid-based transmission to cause the catheter with an MR-based tracking unit mounted to its tip to perform at least one of push forward, pull backward, rotate clockwise, rotate counterclockwise, bend to the right, and bend to the left and wherein the actuators include a master or slave actuator, and wherein the master or the slave actuator comprises two or more piston-actuators, each piston actuator using at least one rolling diaphragm for fluid sealing and having a gear or a flexible connection to transfer translational motion to bi-directional rotation;

wherein the MR-based tracking unit includes an RLC coil circuit, the MR-based tracking unit being switchable between multiple states, such that the MR-based tracking unit, in one state appears as a bright spot in MM scanned images and in another state provides positional information;

using the remote control located outside of the bore of the MM device to direct operation of the actuators so as to move the catheter about the patient's body; operating the MRI device to generate intra-operative MRI image data;

creating a 3-D anatomical roadmap and locating the tracking unit relative to anatomical features of a patient in which the catheter is placed based on the intra-operative MRI image data and wherein 3-D tracking coordinates are the same as an MR image coordinate system; and displaying an endoscopic image view from the end of the catheter with tracked positional data based on the intra-operative MR tracking and imaging.

24. The method of robotically guiding a flexible catheter instrument using MM data of claim 23 further including the step of using an adaptive kinematic control framework.

\* \* \* \* \*